(12) United States Patent
Hahn et al.

(10) Patent No.: US 6,810,713 B2
(45) Date of Patent: Nov. 2, 2004

(54) METHOD FOR HANDLING AND DELIVERING FLUID ON A LAB-ON-A-CHIP

(75) Inventors: Jong Hoon Hahn, Gyeongsangbuk-Do (KR); Kwanscop Lim, Gyeongsangbuk-Do (KR); Kihoon Na, Gyeonggi-Do (KR); Suhyeon Kim, Seoul (KR); Je-Kyun Park, Seoul (KR)

(73) Assignee: LG. Electronics Inc., Seoul (KR)

( * ) Notice: Subject to any disclaimer, the term of this patent is extended or adjusted under 35 U.S.C. 154(b) by 0 days.

(21) Appl. No.: 10/195,320

(22) Filed: Jul. 16, 2002

(65) Prior Publication Data

US 2003/0026719 A1 Feb. 6, 2003

(30) Foreign Application Priority Data

Jul. 24, 2001 (KR) ........................................ 2001-44514

(51) Int. Cl.[7] .............................. G01N 1/00; G01N 1/14; G01N 30/32; F04B 43/04; F04B 43/12
(52) U.S. Cl. .................... 73/23.35; 417/476; 417/477.1; 436/180
(58) Field of Search ........................ 435/5, 6, 7.1, 7.21, 435/287.2; 417/475, 476, 477.1, 477.7; 73/23.35; 436/180; 222/207; 257/200

(56) References Cited

U.S. PATENT DOCUMENTS

| | | | | |
|---|---|---|---|---|
| 3,740,173 | A | * | 6/1973 | Natelson ..................... 417/475 |
| 5,269,443 | A | * | 12/1993 | Lancaster .................... 222/207 |
| 6,203,296 | B1 | * | 3/2001 | Ray et al. ................. 417/477.7 |
| 2002/0037499 | A1 | * | 3/2002 | Quake et al. ................... 435/5 |
| 2002/0127736 | A1 | * | 9/2002 | Chou et al. .................. 436/180 |
| 2003/0008308 | A1 | * | 1/2003 | Enzelberger et al. .......... 435/6 |
| 2003/0025129 | A1 | * | 2/2003 | Hahn et al. .................. 257/200 |
| 2003/0027225 | A1 | * | 2/2003 | Wada et al. ................ 435/7.21 |
| 2003/0040105 | A1 | * | 2/2003 | Sklar et al. ............... 435/287.2 |
| 2003/0096310 | A1 | * | 5/2003 | Hansen et al. ............... 435/7.1 |

FOREIGN PATENT DOCUMENTS

| | | | |
|---|---|---|---|
| DE | 198 42-016 | 3/2000 | |
| DE | 19842016 | * 3/2000 | ............. F04C/5/00 |
| EP | 0 779 436 | 6/1997 | |
| EP | 1 065 378 | 1/2001 | ................. 436/180 |

OTHER PUBLICATIONS

Gregory T. A. Kovacs et al., "Silicon Micromachining: Sensors to Systems," *Analytical Chemistry News & Features* (vol. 68: No. 13), Jul. 1, 1996, pp. 407–412.

D. Jed Harrison et al., "Micromachining a Miniaturized Capillary Electrophoresis–Based Chemical Analysis System on a Chip," *Science*, vol. 261, Aug. 13, 1993, pp. 895–897.

Stephen C. Jacobson et al., "Precolumn Reactions with Electrophoretic Analysis Integrated on a Microchip," *Analytical Chemistry*, vol. 66: No. 23), Dec. 1, 1994, p. 4127–4132.

(List continued on next page.)

*Primary Examiner*—Daniel S. Larkin
(74) *Attorney, Agent, or Firm*—Morgan, Lewis & Bockius LLP

(57) ABSTRACT

Various kinds of fluid can be handled and delivered accurately in infinitesimal amounts through microchannels formed in an elastic polymeric substrate by periodically squeezing selective portions of the microchannel using a rotor to apply an external force on the elastic substrate. The delivery rate of the fluid is in the range from pL/sec to mL/sec determined by the rotation speed of the rotor which presses the microchannels and the dimensions of the microchannel. Regardless of physical properties of the fluid to be delivered, various kinds of fluids can be accurately delivered through the microchannels in the desired amount.

20 Claims, 10 Drawing Sheets

OTHER PUBLICATIONS

Paul C.H. Li et al., "Transport, Manipulation, and Reaction of Biological Cells On–Chip Using Electrokinetic Effects," *Analytical Chemistry* (vol. 69: No. 8), Apr. 15, 1997, pp. 1564–1568.

Martin U. Kopp et al., "Chemical Amplification: Continuous–Flow PCR on a Chip," *Science*, vol. 280, May 15, 1998, pp. 1046–1048.

Helene Andersson et al., "A Valve–Less Diffuser Micropump for Microfluidic Analytical Systems," *Sensors and Actuators*, vol. B72, 2001, pp. 259–265.

Nam–Trung Nguyen et al., Miniature Valveless Pumps Based on Printed Circuit Board Technique, *Sensors and Actuators*, vol. A88: Issue 1, Jan. 20, 2001, pp. 104–111.

Kazuo Kosokawa et al., Handling of Picoliter Liquid Samples in a Poly(dimethylsiloxane)–Based Microfluidic Device, *Analytical Chemistry*, vol. 71, No. 20, Oct. 15, 1999, pp. 4781–4785.

W.K. Schomburg et al., "Active Valves and Pumps for Microfluidics," *Journal of Micromechanics and Microengineering*, vol. 3, 1993, pp. 216–218.

Sebastian Böhm, "An Electrochemically Acutated Micropump for Use in a 'Push–Pull' Microdialysis Based In–Vivo Monitoring System," *Tranducers '99: Digest of Technical Papers*, vol. 2, Jun. 7–10, 1999, pp. 880–881.

"Monolithic Microfabricated Valves and Pumps by Multilayer Soft Lithography", Unger, M.A., et al. Science, vol. 288, Apr. 7, 2000, pp 113–116, XP002259067.

*From Micro– to Nanofabrication with Soft Materials:*, Quake, S.R., et al., Science, vol. 290, Nov. 24, 2000, pp 1536–1540, XP002259068.

"Soft Litghography", Xia, Y., et al., Angewandte Chemie, International Edition, Verlag Chemie, Weinheim De, vol. 37, 1998, pp 551–575, XP000985399.

\* cited by examiner

SILICON SUBSTRATE

NEGATIVE PHOTOSENSITIZING LAYER

ULTRAVIOLET RAYS
PHOTOMASK

MOLD

PDMS PREPOLYMER

FIRST PDMS LAYER

FIRST PDMS LAYER
SECOND PDMS LAYER

PROSPEVTIVE VIEW

FRONT VIEW

METHOD FOR HANDLING AND DELIVERING FLUID ON A LAB-ON-A-CHIP

BACKGROUND OF THE INVENTION

1. Field of the Invention

The present invention relates to a method and device for accurately handling and delivering infinitesimal amounts of fluid in an elastic polymeric substrate of microfluidic devices used in chemical and biochemical analyses, syntheses and detection. The method and device deliver fluid in microchannels formed within an elastic polymeric substrate by using a rotor to apply external force onto the elastic polymeric substrate so that the fluid in the microchannels is forced therethrough.

2. Description of the Background Art

As science and technology develops, interest about component miniaturization and process automation is increasing. Miniaturization reduces the size and weight of an apparatus and reduces the amount of electricity needed for its operation, resulting in the development of portable experimental equipment, such as microfluidic devices. Also, the amount of samples or reagents needed for experiments is substantially reduced and accordingly, experiments using costly samples or reagents can be conducted more efficiently. By automation, a number of processes in conducting experiments can be conducted automatically not by manual labor but by mechanical means. Generally, experiments conducted in laboratories are mainly conducted by performing respective independent processes in parallel or in order. Such processes may require much labor and time. Accordingly, continuity and efficiency are reduced and inaccuracy of experiments increases. Therefore, if automation of experiments is achieved, continuity and efficiency of the experiments are increased, thus the required labor and time can be minimized while accuracy of the experiments is improved.

As micromachining develops together with semiconductor technology, research to achieve miniaturization and automation simultaneously is in process. As an example of such research, the so-called "Lab-on-a-chip" has been developed. Lab-on-a-chip is a chemical microprocessor made by integrating many kinds of apparatuses on a substrate (chip) having a dimension of several centimeters being made of glass, silicone or plastic using photolithography or micromachining used generally in semiconductor technology, and allows automated experiments to be conducted with high speed, high efficiency and low cost (Kovas, Anal. Chem. 68 (1996) 407A-412A). By miniaturizing and integrating many apparatuses onto a chip needed for experimentation and by automating the respective experiment processes to be conducted consecutively, experiments can be conducted more efficiently. Recently, as a result of new technological advances, satisfactory results in developing new medicines and new materials have been obtained by searching, through hundreds of thousands of chemical compound libraries to yield an approach for probable problem-solving solutions. Accordingly, research for compiling and analyzing chemical compound libraries using combinatorial chemical methods are being conducted. To conduct such research, trials to develop experimental methods for synthesizing or analyzing various kinds of samples using a lab-on-a-chip enabling high speed, high efficiency, low cost, miniaturization and automation, are in progress.

As miniaturization and automation are progressed, necessity of new technologies is on the rise because conventional methods used to handle and deliver solutions can not be applied appropriately to provide the necessary infinitesimal amounts of solution transfer needed for experiments. Conventional methods for delivering solutions are inappropriate for delivering infinitesimal amounts of solution due to many factors such as minimum delivery amount or delivery conditions. Also, factors which are not problematic in delivering large amounts of solution may cause serious problems when delivering infinitesimal amounts of solution. For example, due to surface tension generated between the delivered solution and the inner walls of the microchannels upon fluid transfer therethrough, the solution can be delivered in an unexpected direction or delivered inefficiently. Also, due to an increase in the so-called "back pressure" generated when the solution flows in the microchannel, pressure for delivery increases undesirably, and accurate amount of delivery is difficult because portions of the solution may vaporize in the microchannel.

As a method to deliver infinitesimal amounts of solution in a microchannel, the most common method employs electric fields. The method of using electric fields can control the flow of solution by using capillary electric osmosis generated when a voltage is applied at both ends of the microchannel filled with the solution without using an additional pump or valve. It is also possible to analyze samples on the chip because separation of the sample using capillary electrophoresis is possible (Harrison, Science 261 (1993) pp.895–897; Jacobson, Anal. Chem. 66 (1994) pp.4127–4132; Li, Anal. Chem. 69 (1997) pp.1564–1568; Kopp, Science 280 (1998) pp.1046–1048). The apparatus for this method is simple and accordingly, this method is used most commonly in the field of delivering solutions in microchannels such as those in a lab-on-a-chip. However, if one or more channels are connected in a complicated manner, controlling the delivery of the solution is difficult. Accurate delivery is also difficult or impossible if various kinds of solutions are delivered because the flow rate of the solution is affected by the physical properties, such as acidity (pH), ionic strength and viscosity, of the solution to be delivered and microchannel surface condition.

In addition to the above method, much research has been conducted to develop a method for accurately delivering an infinitesimal amounts of solution for microfluidic devices. First, there is a method for delivering a solution by connecting an external micropump to a microchannel. For this method, a peristaltic pump, injector pump or HPLC pump is used, or a method using compressed air is also applied (Hosokawa, Anal. Chem. 72(1999) pp.7481–4785). However, such methods can only deliver solutions in the amount of microliters and accordingly, they are inappropriate for many fields such as the lab-on-a-chip technique, which handle and deliver infinitesimal amounts of solution in the level of nanoliters or picoliters. Also, waste of unnecessary reagents or samples is increased since the fluid must be filled from the pump to the microchannels to connect the external micropump with the microchannels of the lab-on-a-chip. Also, the fluid can leak from the portion connecting the chip and the external micropump since the pressure for delivering the solution is undesirably generated at the external portions of the chip and accordingly, complicated and sophisticated design and assembly are necessary.

Research of various techniques to deliver a solution by directly embodying a micropump in a chip are actively pursued, to overcome disadvantages in the method of connecting an external micropump with a microchannel in the chip. As the result of such research, many methods were reported, including a method of using piezoelectric material having a diaphragm in the chip (Andersson, Sens. Actuators B72(2001) pp.259–265; Nguyen, Sens. Actuator A (2001), pp.104–111), an on chip-type diaphragm pump for delivering the solution by vibrating the diaphragm using air pressure (Scomburg, J. Micromech. Microeng. 3(1993) pp.216–218), a method for delivering the solution by making air bubbles in the microchannel through a electrochemical reaction therein (Bohm, Proceedings of the Transducers, Sendai, Japan, 1999. pp.880–881) and the like. However, to accommodate such methods, manufacturing an appropriate chip structure is difficult since additional elements or devices must be embodied to deliver the solution in the chip. Also, conventional devices such as electroosmotic pump are inappropriate for delivering various kinds of solutions because the physical properties of the delivered solutions affect accurate fluid delivery.

SUMMARY OF THE INVENTION

Therefore, the present invention provides a method and device for handling and delivering fluid in an elastic polymeric substrate, and for delivering various kinds of fluids in an infinitesimal amount in the range from picoliters to milliliters at a constant rate regardless of the physical properties of the fluid in the substrate having a microchannel therein. Additional external devices or structures on the substrate are not required to handle and deliver the fluid.

A gist of the present invention involves the identification of conventional art problems related to handling and delivering accurate and infinitesimal amounts of fluid through microchannels. In one embodiment, the present invention solves such problems by periodically applying an external (mechanical) force onto a polymeric substrate using a rotor to compress the microchannel having fluid therein, and periodically releasing the applied external force from the substrate to decompress the microchannel like peristaltic pump to deliver fluid therethrough.

In other words, in accordance with the present invention, a fluid is transferred through the microchannel by periodically squeezing selective portions thereof, and a chemical operation is performed by using the transferred fluid.

The foregoing and other features, aspects and advantages of the present invention will become more apparent from the following detailed description when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings. Here, the term "substrate" has an identical meaning with the term "chip" and are used interchangeably to describe structural aspects of the present invention.

Figure 1A:
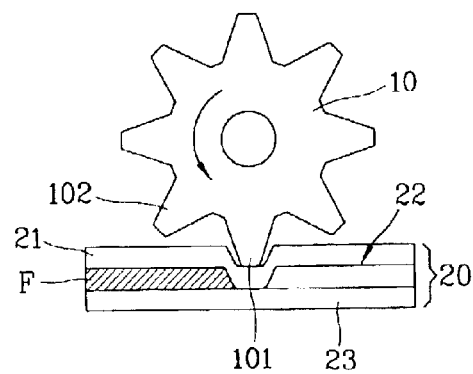
FIGS. 1A to 1C show the fundamental principles of the present invention and the process of how a fluid in a microchannel is delivered by the gear-like teeth of a rotor, which press the microchannel.
Figure 1B:
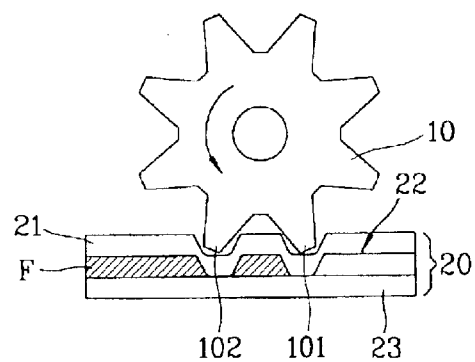
Figure 1C:
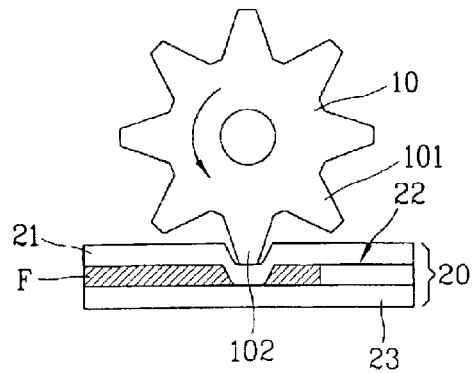

The principle of how fluid is delivered in the present invention is shown in FIGS. 1A to 1C. On an elastic polymeric substrate 20, as shown in FIGS. 1A to 1C, the fluid F is delivered by applying an external (mechanical) force on a portion of the substrate above a microchannel 22 using a rotor 10 with a toothed wheel shape. The rotor 10 is rotated to sequentially add pressure on the microchannel 22 formed within the substrate 20. As shown in FIG. 1A, after pressing a first portion of the microchannel 22 with the first gear tooth 101 of the rotor 10, the fluid F in the microchannel 22 is first compressed by an inner wall of the microchannel 22. As the rotor 10 rotates, a second gear tooth 102 of the rotor 10 also begins to apply pressure along a subsequent portion of the microchannel 22 with the first gear tooth 101 still compressing the first portion of the microchannel 22 as shown in FIG. 2B. Thereafter, the first gear tooth 101 moves away from the elastic polymeric substrate surface while the second gear tooth 102 continues to apply pressure on the microchannel 22, as shown in FIG. 1C. Thereafter, the subsequent gear teeth continue to apply periodic pressure on the microchannel 22 through the substrate 20 so that the fluid F therein is delivered therethrough. During this process, the rotational shaft of the rotor 10 can be positioned parallel to the surface of the substrate 20 and across the microchannel 22 above the substrate 20. The rotational shaft can also be moved vertically towards or away from the substrate 20 to adjust the amount of external pressure applied from the rotor 10. When the rotor 10 rotates, the shaft of the rotor 10 preferably does not move in the longitudinal direction along the microchannel 22, as the fluid F in the microchannel 22 is delivered along the rotational direction of the rotor 10 as the gear teeth apply pressure to the substrate 20. The external force applied by the rotor 10 onto the microchannel 22 is only limited by the diameter size of the rotor 10 because the rotor 10 itself does not move in the longitudinal direction along the microchannel 22 and thus, the fluid F can be continuously transferred in one direction as long as fluid is continuously provided into the microchannel 22. In other words, the rotor 10 itself needs not to be displaced to move the microchannel 22. The rotation of a rotor 10 held at a fixed position above the substrate 20 allows fluid transfer by periodically squeezing selective portions of the microchannel 22. The amount and delivery rate of the fluid are generally determined by the internal size of the microchannel 22 and the rotation speed of the rotor 10, which presses the microchannel 22. A characteristic of the present invention is that a means for delivering fluid is not included in the substrate itself. Therefore, it is easy to design and manufacture the substrate for fluid handling because no complicated manufacturing processes for embodying structures or devices in the substrate to deliver the fluid are necessary. By such characteristics, the present invention can be directly applied to various types of substrate or chip structures having microchannels formed therein.

The method of the present invention for handling and delivering fluid can be described in more detail with reference to the following examples and embodiments, but the present invention is not limited to these examples.

EXAMPLES AND EMBODIMENTS

1. An Apparatus for Delivering Fluid in an Elastic Substrate

Figure 2:
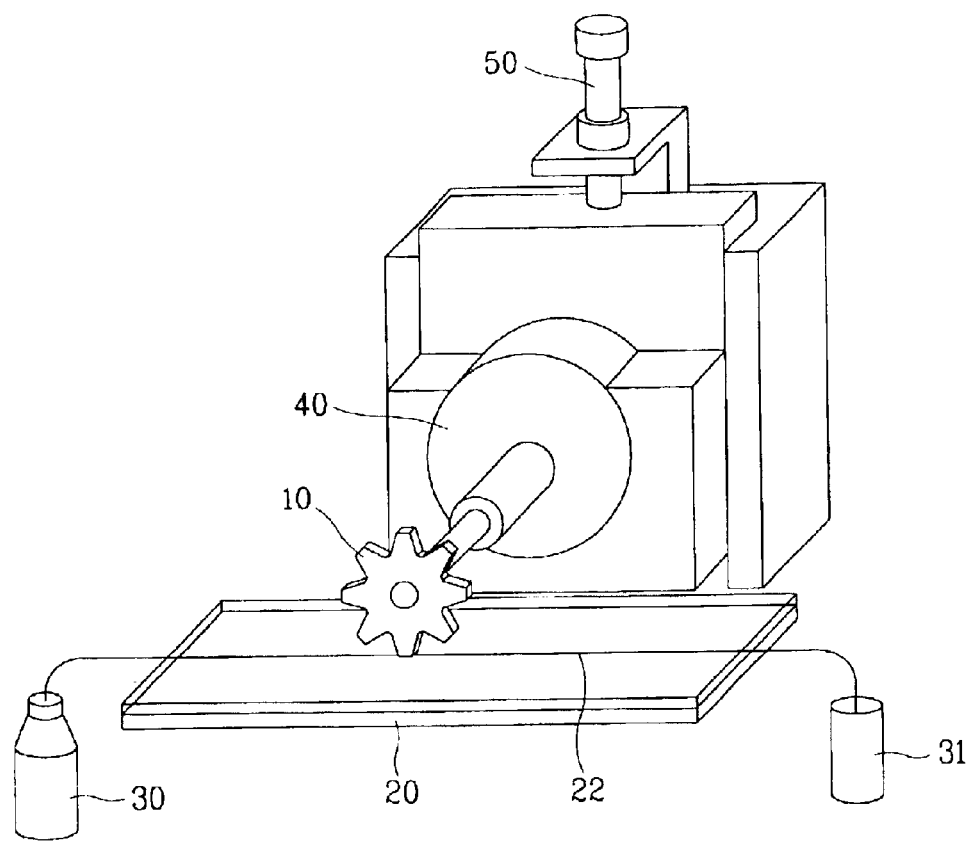
FIG. 2 is an apparatus for delivering an infinitesimal quantity of fluid according to Example 1.
Figure 3A:
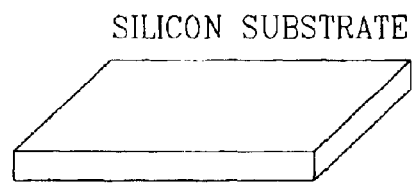
FIG. 3 shows a method for manufacturing a chip having a microchannel therein made of poly(dimethylsiloxane) (hereinafter referred to as "PDMS"), including the steps of (A) providing a silicone substrate, (B) spin-coating a negative photosensitizer on the substrate, (C) covering a photo mask and exposing the substrate to ultraviolet rays, (D) forming a mold by removing a portion which is not exposed using a developing solution, (E) pouring a PDMS prepolymer to the mold and hardening in an oven, (F) removing the mold and then making a fluid inlet by making a hole in the PDMS layer and (G) attaching a new PDMS layer to form a chip having a microchannel between the two PDMS layers.
Figure 3B:
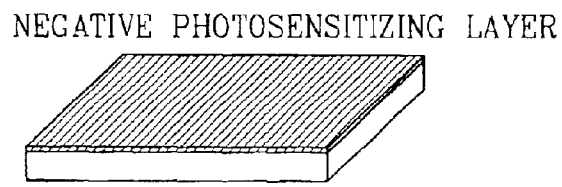
Figure 3C:
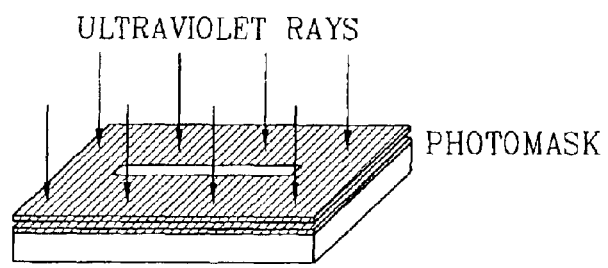
Figure 3D:
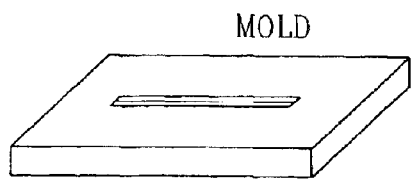
Figure 3E:
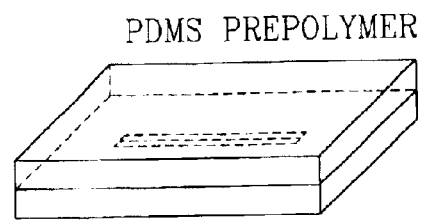
Figure 3F:
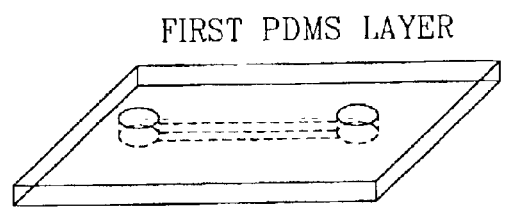
Figure 3G:
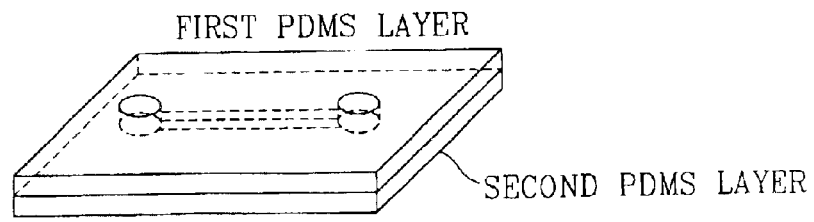

By using the present invention, an example of an apparatus for accurately delivering fluid F in the substrate 20 is shown in FIG. 2. A rotor 10 shaped in the form of a "toothed wheel" is used to press the microchannel 22 by applying an external force on the microchannel 22 in the substrate 20, as the rotor 10 rotates by means of a stepping motor 40. The rotor 10 connected with the stepping motor 40 can be installed in a manual z-axis translational device 50 and accordingly, the rotor 10 can press the microchannel 22 by applying an external force onto the substrate 20 by manually operating the z-axis of the z-axis translational device 50 to lower or raise the rotor 10 position above the substrate 20. The means for applying external force on the substrate 20 can be manual z-axis translational devices as in this Example. The rotor 10 positioning can also be automated by using an additional motor, pump, electromagnet or the like. As a means for rotating the rotor 10, a DC motor or servomotor as well as a stepping motor can be used. To supply the desired fluid F continuously, a device for storing the fluid can be included in the substrate 20 or in case the amount of fluid exceeds the limitation of the internal capacity of the substrate 20, an external storage container 30 can be additionally connected with the microchannel 22 through a connection pipe or the like. Also, an outlet container 31 can be attached to the other end of the microchannel 22 for receiving the delivered fluid.

FIG. 3 is an example of the method for manufacturing a microchannel chip made of PDMS, which is a kind of elastic polymer. First, the microchannel substrate is manufactured by the following method including the steps of making an embossing mold on a silicone substrate having embossed portions in the form of the desired microchannel to be formed (FIG. 3D) by photolithography techniques used in semiconductor manufacturing processes (FIG. 3A, 3B and 3C), pouring a pre-polymer material (for example, Sylgard 184, Dow Corning; A:B=10:1) for making a first PDMS layer to the embossing mold, hardening the resultant material in an oven at a temperature of about 75° C. (FIG. 3E), removing the embossing mold and trimming the substrate as desired, forming a hole having a diameter of about 3 mm at the end portions of the microchannel to be formed (FIG. 3F) and completing the formation of the capillary-like microchannel by placing and bonding a second PDMS layer on the lower surface of the first PDMS layer (FIG. 3G). For the substrate to have proper microchannels, in addition to PDMS, any type of material can be used on condition that it allows blockage of the microchannel when pressed. Generally, it is desirable that polymeric materials such as rubber, silicone type rubber or plastics having certain elasticity are used. As methods of making a microchannel in the substrate, in addition to a method of hardening after pouring a pre-polymer material like PDMS to a mold as described above, methods of directly pressing a flat substrate surface with a embossed mold, applying hot embossing to the substrate, using mechanical means to process the substrate and forming microchannels with light or heat using laser energy or other methods of applying light or heat energy can be used.

Various types of fluids including liquids and gases can be delivered through the microchannels in accordance with the present invention. By filling the fluid inlet connected to the microchannel with the desired fluid and by operating the rotor to apply pressure on the substrate portions above the microchannel, the air in the microchannels first is discharged and the void created in the microchannel is filled by the fluid from the inlet to thereby allow continuous and accurate fluid transfer through the microchannel. Accordingly, it is not necessary to pre-fill the microchannel with the desired fluid to be delivered. The volume of the delivered fluid in the apparatus is determined by the size (e.g., the diameter or cross-section) of the microchannel in the substrate surface area pressed by the rotor, the rotation speed of the rotor and the structure of the rotor. The rotation speed of the rotor is determined by the rotation speed of the stepping motor or other driving means connected with the rotor. Namely, the rotation speed of the rotor is determined by an angular resolution of the stepping motor and a frequency of a pulse signal input to the stepping motor. The stepping motor used in the present invention can have an angular resolution of 1° per pulse, and the pulse signal can allow the rotation speed of the rotor to be controlled by inputting signals of various frequencies between several Hz and hundreds of Hz to generate a desired rotational speed of the rotor.

The device according to the present invention capable of continuously supplying fluid through microchannels has an advantage in that it can be applied as a simple device in various fields requiring chemical compounds and mixtures to be supplied and/or handled continuously. The amount of fluid supply can be easily controlled according to described conditions, in addition to supplying fluid at a constant rate for a prolonged period of time. The present invention can be applied to numerous devices including devices for supplying medical or other types of fluids to humans, animals or plants, for supplying compounds or mixtures in chemical or biological processing, and for supplying a culture solution in a cell or microbe cultivator, just to name a few.

2. A Method for Delivering Fluid in an Elastic Single Microchannel Substrate

Figure 4:
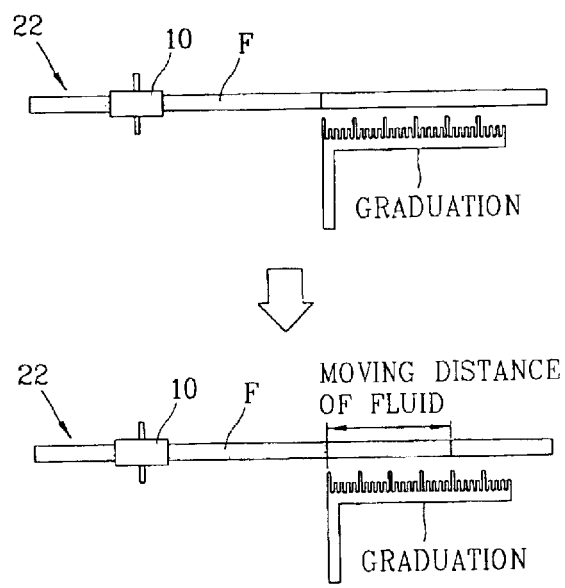
FIG. 4 shows experimental methods of Examples 2 and 3.
Figure 5:
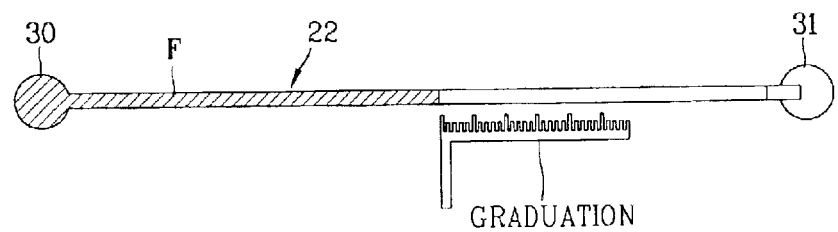
FIG. 5 shows a portion of a single channel chip having graduations of Examples 2 and 3.
Figure 6:
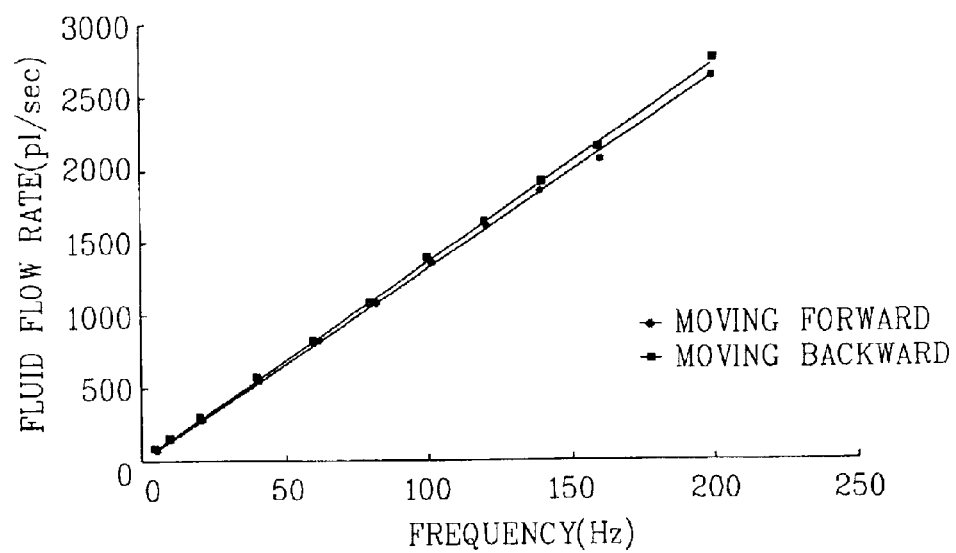
FIG. 6 shows a delivery rate of a fluid according to the a pulse signal input to a stepping motor for rotating a rotor of Example 2.

Fluids can be accurately and efficiently handled/delivered through microchannels using the apparatus of FIG. 2 and the single microchannel substrate. FIG. 4 illustrates the method for delivering fluid in a single microchannel substrate made of elastic material. The delivery rate of the fluid can be measured with a velocity sensor but in the present example, the delivery rate was calculated by measuring the fluid moving time upon observing the moving distance of the boundary between the fluid F and the air in the microchannel 22 using a monitor connected with a Charged-Coupled Device (CCD) camera. The single microchannel substrate as described in FIG. 5 can be placed on the apparatus as described in FIG. 2. The single microchannel substrate in FIG. 5 has a microchannel having a width of about 50 $\mu$m, depth of about 30 $\mu$m and length of about 4 cm and has graduations formed on the side portion of the microchannel 22 to observe fluid F flow within the microchannel 22. The manual z-axis translational device 5 can be operated to control the rotor 10 for pressing the microchannel substrate. The fluid F is delivered through the microchannel 22 by rotating the rotor 10 connected to the stepping motor. The process is preferably performed while the user observes the process by a CCD camera. When the fluid F reaches the central portion of the microchannel 22, the stepping motor is stopped, and the input signal frequency of the stepping motor is set to correspond with the desired rotation speed. After setting the input signal frequency, while rotating the rotor 10 at a predetermined speed, the time required for the boundary surface between the fluid F and air to pass two graduations formed at uniform intervals along the microchannel 22 can be measured by a stopwatch. FIG. 6 is a graph showing the delivering speed of the fluid F according to the rotation speeds of the rotor 10. As shown in FIG. 6, the delivery rate is from about 50 picoliters/sec to about 2.5 nanoliters/sec. If the performance of the motor which rotates the rotor 10 is improved and the friction between the rotor 10 and the substrate 20 is reduced by for example, applying lubricant on the substrate 20, the rotation speed of the rotor 10 can be increased and therefore the fluid delivery rate can be increased even further.

The delivery rate of the fluid F can also be adjusted by varying the width and the depth of the microchannel 22. For example, when using a substrate 20 having a microchannel 22 width and depth of about 10 $\mu$m and 3 $\mu$m, respectively, the delivery rate is decreased to 1/50 from the example in FIG. 6 and accordingly, by the same method as in FIG. 4, the fluid delivery rate of about 1 picoliters/sec to about 50 picoliters/sec can be obtained. Also, when using a substrate 20 having a microchannel 22 width and depth of about 3 mm and 1 mm, respectively, the delivery rate of the fluid can be adjusted from about 0.1 $\mu$L/sec to about 5 $\mu$L/sec. The range of delivery rate can be controlled by adjusting the width and the depth of the microchannel 22 according to the desired usage. Also, the delivery rate of the fluid F can be controlled by adjusting the rotation speed of the rotor 10 within the range of delivery rate.

3. A Method of Delivering Fluids Having Various Kinds of Characteristics Through a Single Channel Substrate Generally, most conventional apparatuses used for accurately delivering infinitesimal amounts of fluids require adjustments to their delivery conditions according to the physical properties of the fluid to be delivered. For example, when using electro-osmosis for fluid delivery, the rate of electro-osmotic flow is changed according to the composition of the solution. Therefore, in order to obtain the desired fluid delivery rate, a calibration procedure must be performed by varying the intensity of the electric field being applied and measuring fluid delivery rate for each intensity level prior to carrying out the desired experiment with the appropriate fluid delivery rate. However, using the present invention, fluids can be delivered at a constant rate despite the different physical properties of the fluid to be delivered, because the fluid is delivered by applying an external force on the microchannel using the device in FIG. 2 and the single microchannel substrate.

Figure 7:
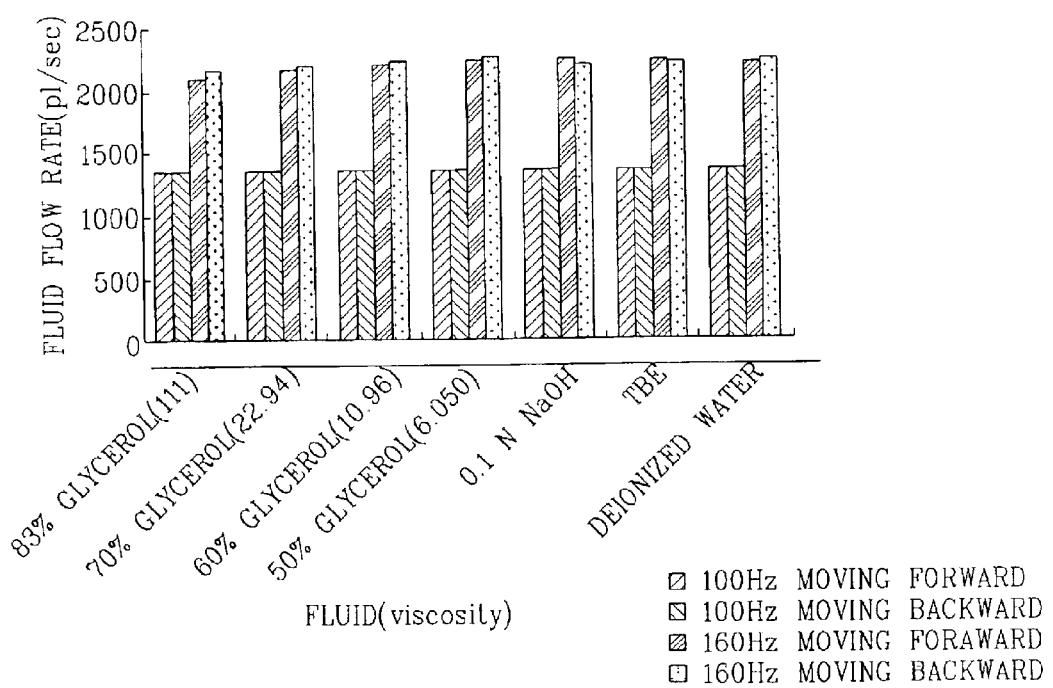
FIG. 7 is a diagram showing the results of delivery of various kinds of fluids.

In Example 3, the experiment is carried out in the same manner as in Example 2, and the single microchannel substrate has a microchannel with a width and depth of about 50 $\mu$m and 30 $\mu$m, respectively. A pulse signal having a frequency of about 100 Hz or 160 Hz was inputted to the stepping motor for rotating the rotor. FIG. 7 is a diagram showing the results of the delivery of various kinds of fluids and shows that the delivery rates of various kinds of fluids having different acidity, viscosity and ionic strength according to two speeds of rotor are the same regardless of the type of fluid.

4. A Method for Reducing Pulsation in the Stream of the Delivered Fluid

The flow stream of the fluid according to the present invention may have a pulsatory characteristic instead of a continuously smooth characteristic. As shown in FIG. 1, this is because the fluid flow is intermittently blocked in the microchannel 22 being periodically pressed regularly by the gear-like teeth of the rotor 10 during fluid delivery. Such pulsation is a disadvantage commonly occurring in conventional micropumps and does not cause a major problem in experiments requiring simple delivery of solution in a certain amount. However, pulsation is a serious problem in applications requiring a continuous stream of fluid being supplied at a constant rate.

Figure 8:
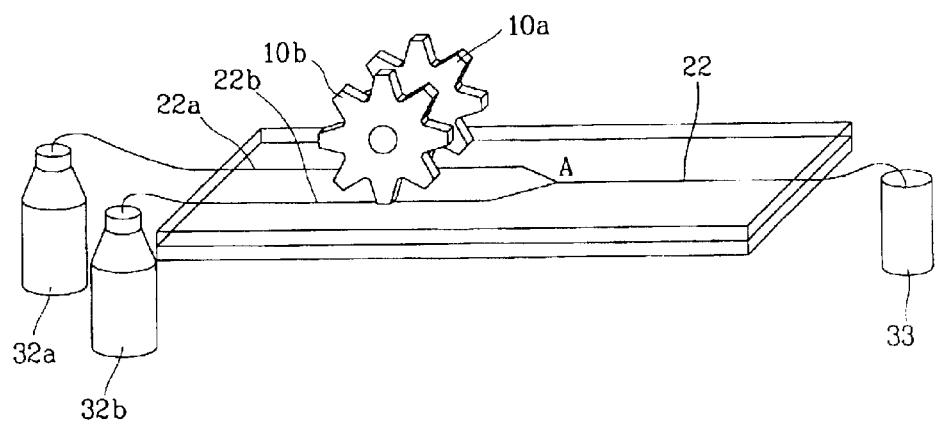
FIG. 8 shows an infinitesimal fluid delivering apparatus, which reduces a pulsating characteristic in a flow of the solution of Example 4.
Figure 9:
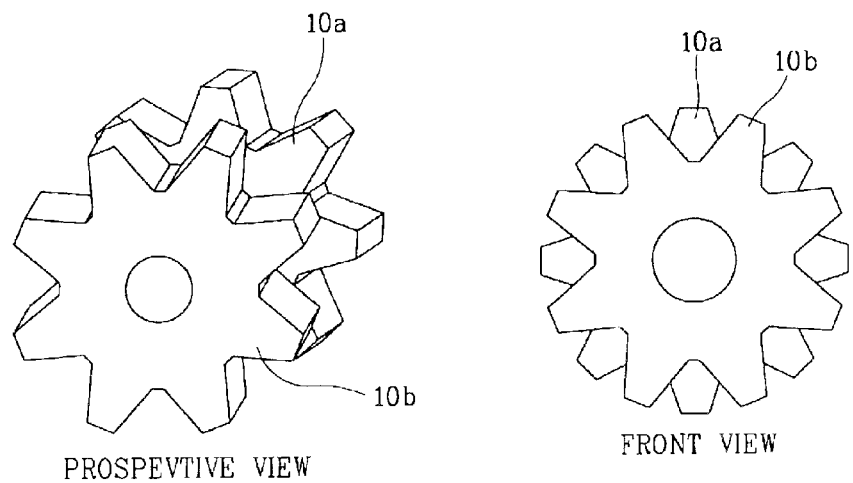
FIG. 9 shows a rotor having a dual-crossing structure used in Example 4.

FIG. 8 shows an apparatus for reducing the pulsatory characteristics in the flow stream of the delivered fluid in accordance with the present invention. With such apparatus, after delivering the fluid through two independent microchannels 22a and 22b by using two rotors 10a and 10b which are of the same type as shown in FIG. 9, the fluid is combined at portion A of the substrate 20 connected with a single microchannel 22. The two rotors 10a and 10b are positioned so that the teeth of one rotor are staggered with those of the other rotor as shown in FIG. 9B. When using two rotors 10a and 10b having a staggered positioning and two microchannels 22a and 22b, each microchannel 22a and 22b provides a pulsatory stream. However, when one microchannel among the two microchannels allows fluid to be delivered at a minimum velocity, the other microchannel allows fluid at a maximum velocity due to the staggered rotors 10a and 10b applying pressure onto their respective microchannels 22a and 22b. As the two fluid streams are then combined at the portion A, the pulsation of the final output stream is reduced. In this manner, the present invention can even be applied to chemical experiments and applications that require a continuous and constant flow of fluid.

5. An Apparatus for Monitoring Samples in Real-time

Figure 10:
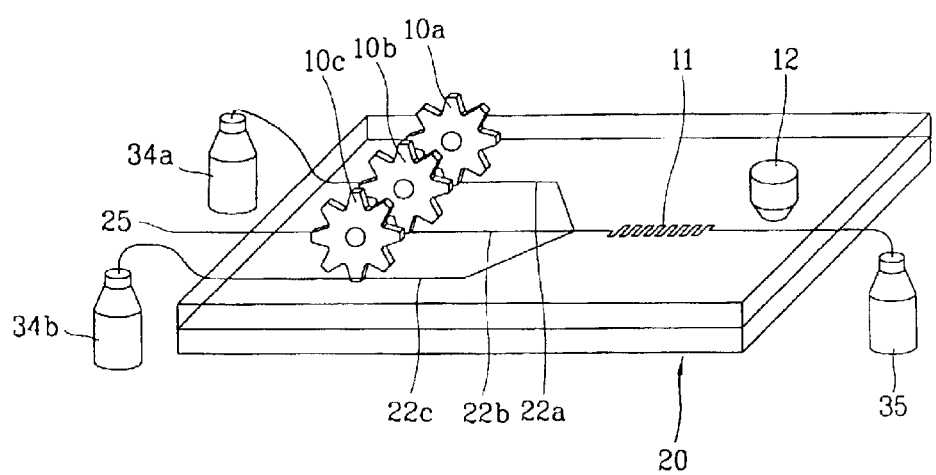
FIG. 10 shows an apparatus for monitoring samples in Example 5.

FIG. 10 shows an apparatus for real-time monitoring of changes in the concentrations of certain components contained in samples. The method can be used in applications requiring real-time monitoring, such as monitoring of the discharging water of a plant, quality management of products made from the fluid or other fluid handling applications. Real-time analysis is performed by introducing the sample to be analyzed into the substrate 20 through the sample inlet part 25 of the apparatus in FIG. 10, after processing to detect the introduced sample by inducing a chemical reaction in the reaction portion 11 using a chemical reagent stored in portions 34a and 34b.

A reaction of a sample and a chemical reagent can take place in one portion of the microchannel 20, i.e., reaction portion 11, as shown in FIG. 10. It is also possible to change the structure of the microchannel 20 so that the sample can react with different chemical reagents in order or in parallel. Also, if a valve-like element is formed in the microchannel, the supply of samples or reagents can be further controlled through the microchannel to deliver continuous or non-continuous amounts. Further, after making the sample move along a microchannel in a non-continuous manner which may appear as a "band" passing through the microchannel, and if a portion of the microchannel (where the band of the sample will pass) is filled or coated with column material for chromatography, the chemical components within the band of the sample can be separated and then detected by a detector 12 positioned in the end portion of the microchannel. In this case, the microchannel 22 can be used in performing analyses like those performed during chromatography.

By independently or compositively using the principles of the present invention as described above, various types of analyzers for chemical compounds can be made. Such analyzers can be used in instruments for developing new medicines, for biochemical analysis, for pre-processing of chemical samples, for analyzing molecules, for analyzing environmental pollutes, for detecting or discriminating of chemical or biochemical weapons, for monitoring of chemical or biological processing, and for medical diagnosing and health examining, just to name a few.

6. An Apparatus for Performing Consecutive Reactions

Figure 11:
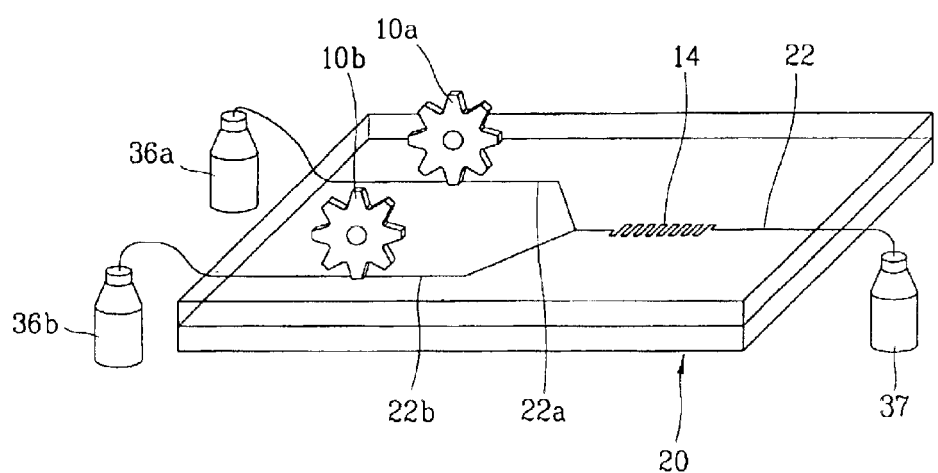
FIG. 11 shows an apparatus which can perform continuous chemical reactions in Example 6.

Generally, in a chemical reaction, a number of independent processes may need to be performed in a step by step sequence. Therefore, to obtain a desired amount of final product, it is necessary to begin each step after calculating the amount of starting material according to the yield of the reaction of each step, to obtain a desired amount of final product. If the desired reaction can be performed continuously, the reaction can be terminated when the desired amount of product is obtained, and accordingly, such apparatus can efficiently perform chemical reactions for many chemical applications. FIG. 11 is a view showing an apparatus, which can continuously perform a desired reaction or reactions in accordance with the present invention.

As previously explained, due to the use of a rotor mounted at a stationary position above the substrate 20 with a microchannel therein, the present invention can continuously introduce chemical reagents into the substrate 20 through the inlet units 36a and 36b, carry out the reaction in the reaction portion 14 and gather the product at the outlet unit 37. In the substrate 20, the processes of extraction, separation and/or purification can be performed to remove by-products from the desired final product of the reaction. The method can be efficiently applied in case a desired amount of substance must be obtained or identical reactions must be repeated continuously. Namely, in producing fine chemicals which does not require any mass production, the synthetic process conventionally performed by manual labor can be replaced by using the method and device of the present invention with a reaction substrate to achieve a so-called "automated small-scale chemical plant". Also, the present invention can be applied to various chemical processes by appropriately modifying the structure of the microchannels in the substrate.

7. A Method for Reducing Friction by Adding a Miniature Rollers to a Rotor

Figure 12:
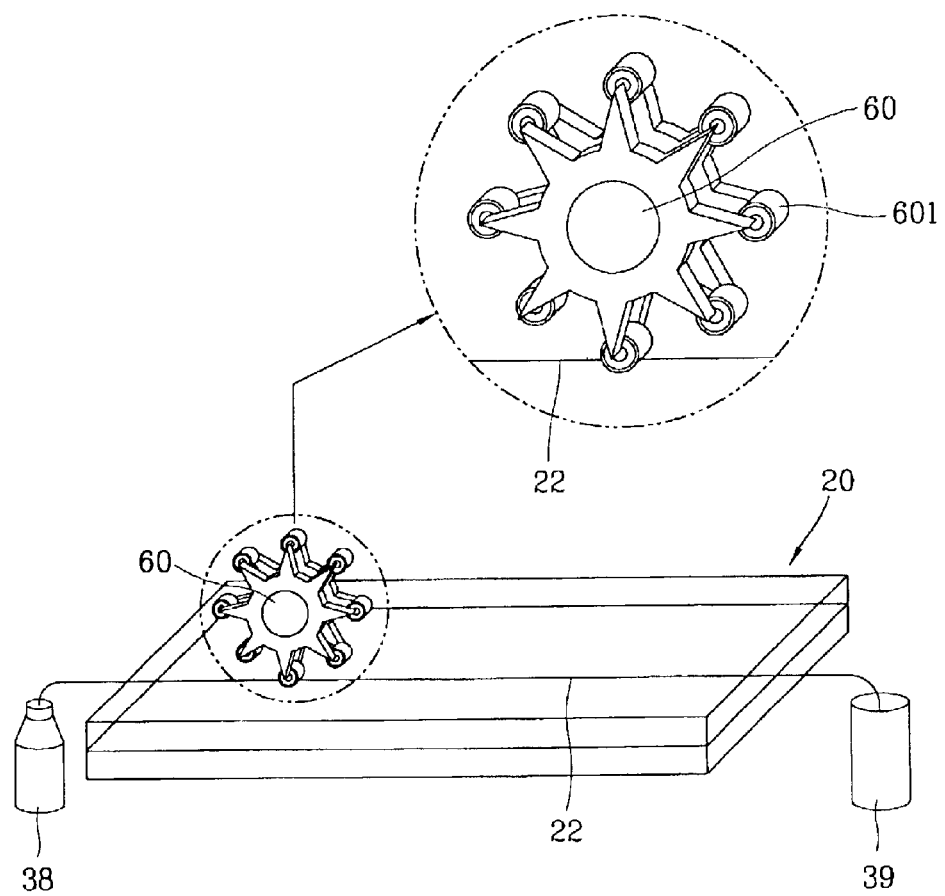
FIG. 12 shows a rotor, which reduces friction with the surface of the chip by using rollers attached on the teeth of the rotor of Example 7.

In case of using a rotor 10 having a toothed wheel shape as described above, the substrate 20 can sometimes be damaged by the friction generated between the teeth of the rotor 10 and the surface of the microchannel substrate 20. Thus, the rotor 10 sometimes can not be rotated as fast a desired. In order to obtain fast delivery rate without damaging the microchannel substrate 20, a modified rotor that can rotate fast enough without damaging the microchannel substrate 20 is necessary. FIG. 12 is a view showing a rotor 60 designed to apply pressure to the substrate 20 above the microchannel 22 using a plurality of miniature rollers 601 operatively connected at the end portion of each tooth of the rotor 60. Accordingly, the friction between the teeth of the rotor 60 and the contact surface on substrate 20 can be minimized, and the rotor 60 can rotate quickly without damaging the substrate 20, thereby to obtain a rapid fluid delivery rate.

According to the present invention, a method and apparatus for efficiently handling and delivering fluids in an infinitesimal amount (in the range of picoliters) up to a small amount (in the range of milliliters) regardless of the kind of fluid can be achieved with a simple structure.

The method and apparatus for handling and delivering fluid in the elastic substrate according to the present invention can be applied as an efficient means for handling and delivering fluids in various fields of technology requiring the use of infinitesimal amounts of fluid. The present invention can be applied in developing new substances by synthesizing many kinds of substances simultaneously through combinatorial chemistry technologies, searching for new medicines by identifying the characteristics of many kinds of substances, life science technology dealing with infinitesimal amounts of physiologically active materials such as enzymes, proteins, DNA, neurotransmitters and the like, developing portable analyzing instruments for detecting and discriminating environmental pollutants or chemical, biological and radiological weapons, and developing household clinical diagnosing instruments.

Particularly, the present invention can be applied when a number of chemical processes, such as synthesis of a substance or analysis of samples, need to be carried out in a substrate, such as the so-called lab-on-a-chip technology which is expected to be rapidly developed in the future. Such technology requires that infinitesimal amounts of fluid be provided efficiently without having to employ a complicated apparatus or structure in the substrate. Designing and manufacturing of the substrate is very simple and consequently, the present invention can contribute to the research and practical use of lab-on-a-chip technology, as well as in many other field of research and development.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A method of causing a fluid to travel within an elastic microchannel present in an elastic substrate by temporarily and periodically deforming a first portion of the microchannel by applying an external force onto the substrate using a rotor having toothed portions to urge the fluid therein towards a second portion of the microchannel.

2. The method of claim 1, wherein the microchannel is periodically deformed by selectively applying and removing the external force to and from the microchannel.

3. A method of handling a fluid comprising:
providing a substrate comprising at least one elastic microchannel formed therein;
transferring a fluid through the microchannel by periodically squeezing a selective portion of the microchannel by applying an external force onto the substrate using a rotor having toothed portions; and
using the transferred fluid for chemical or biological processing.

4. The method of claim 3, wherein the transferring of fluid is achieved by applying and releasing the external force to and from the substrate to compress or decompress the microchannel therein.

5. The method of claim 3, wherein the transferring of fluid is continuously performed by continuously supplying an external fluid through a path connected with the microchannel into the microchannel to allow continuous chemical processes to be performed.

6. The method of claim 3, wherein the transferring of fluid results in a non-uniform fluid flow.

7. The method of claim 6, wherein the non-uniformity of fluid flow is minimized by combining the non-uniform fluid flow from two different microchannels into a single microchannel to obtain a relatively uniform fluid flow.

8. The method of claim 3, wherein the chemical or biological processing comprises separation, analysis or synthesis of a chemical compound or mixture by carrying out at least one process of reaction, separation, mixing, extraction, purification, concentration and titration.

9. The method of claim 3, wherein the chemical or biological processing is using a portion of the microchannel as a column of chromatography for separating a chemical compound.

10. The method of claim 3, wherein a lubricant is applied on portions of the substrate where the external force is applied.

11. The method of claim 3, wherein the fluid being transferred comprises at least one of a gas, an aqueous solution, an organic solution, an inorganic solution, and a solution or gas containing particles therein.

12. A microfluidic device for handling a fluid, the device comprising:
a substrate having at least one elastic microchannel formed therein which are independent or connected with each other;
a rotor having teeth-like portions which is a transfer element in operative contact with the substrate to transfer a fluid through the microchannel by periodically squeezing a selective portion of the microchannel by applying an external force onto the substrate; and
a processing element operatively connected with the microchannel to use the fluid transferred by the transfer element for chemical or biological processing.

13. The device of claim 12, wherein the rotor is positioned onto the substrate to periodically apply and release the external force to and from the substrate to compress or decompress the microchannel therein for transferring a fluid therethrough.

14. The device of claim 12, wherein the rotor transfers the fluid continuously by continuously supplying an external fluid through a path connected with the microchannel into the microchannel to allow continuous chemical processes to be performed by the processing element.

15. The device of claim 14, wherein the rotor transfers the fluid in a non-uniform fluid flow manner.

16. The device of claim 15, wherein two separate rotors are positioned above two separate microchannels being connected to a common microchannel, whereby the two separate rotors operate in an alternating manner so that a non-uniform fluid flow of one microchannel comprises a non-uniform fluid flow of another microchannel when fluid is combined in the common microchannel.

17. The device of claim 15, wherein the rotor further comprises a roller operatively attached to each of the teeth-like portions to minimize friction upon contacting the substrate.

18. The device of claim 12, wherein the processing element is a portion formed within the substrate and connected with at least one microchannel to allow separation, analysis or synthesis of a chemical compound or mixture by carrying out at least one process of reaction, separation, mixing, extraction, purification, concentration and titration.

19. The device of claim 12, wherein the processing element is a portion of the microchannel being used as a column of chromatography for separating a chemical compound.

20. The device of claim 12, which is a component of a lab-on-a-chip system, a chemical compound analyzer, a chemical compound synthesizer or a medical instrument.

* * * * *